(12) United States Patent
Sugarman et al.

(10) Patent No.: US 6,307,372 B1
(45) Date of Patent: Oct. 23, 2001

(54) METHODS FOR HIGH THROUGHPUT CHEMICAL SCREENING USING MAGNETIC RESONANCE IMAGING

(75) Inventors: Jeffrey H. Sugarman, Los Altos; Joshua M. Star-Lack, Palo Alto, both of CA (US)

(73) Assignee: Glaxo Wellcome, Inc., Research Triangle Park, NC (US)

( * ) Notice: Subject to any disclaimer, the term of this patent is extended or adjusted under 35 U.S.C. 154(b) by 0 days.

(21) Appl. No.: 09/432,492

(22) Filed: Nov. 2, 1999

(51) Int. Cl.[7] ................................................. G01V 3/00
(52) U.S. Cl. ............................................. 324/321; 422/67
(58) Field of Search ..................................... 324/300, 321, 324/322, 318, 312, 314, 306, 307, 309; 422/67, 102; 436/173

(56) References Cited

U.S. PATENT DOCUMENTS

| | | | |
|---|---|---|---|
| 4,999,580 | 3/1991 | Meyer et al. | 324/309 |
| 5,552,709 | * 9/1996 | Anderson | 324/321 |
| 5,652,516 | 7/1997 | Adalsteinsson et al. | 324/309 |
| 5,653,233 | 8/1997 | Pelc et al. | 128/653.2 |
| 5,856,744 | 1/1999 | Block et al. | 324/309 |
| 6,027,941 | * 2/2000 | Jarvic et al. | 436/173 |
| 6,036,920 | * 3/2000 | Pantoliano et al. | 422/67 |
| 6,136,274 | * 11/2000 | Nova et al. | 422/102 |

OTHER PUBLICATIONS

Wehrli, Felix W., Ph.D., "Introduction to Fast Scan Magnetic Resonance", General Electric Company, GE Medical Systems, 1990.

Keller, Paul J., Ph.D., "Basic Principles of Magnetic Resonance Imaging", General Electric Company, GE Medical Systems, 1991.

Stahl, Wilhelm, "What is the Future of High Throughput Screening?", *Journal of Biomolecular Screening*, vol. 4, No. 3, 1999.

Wehrli, Felix W., "The Origins and Future of Nuclear Magnetic Resonance Imaging", *Physics Today*, Jun. 1992.

* cited by examiner

*Primary Examiner*—Louis Arana
(74) *Attorney, Agent, or Firm*—Townsend and Townsend and Crew LLP (57) ABSTRACT

A screening method is provided that comprises the steps of performing an assay in which one or more chemicals and/or entities are present in a mixture to produce an outcome. A static magnetic field $B_0$ is applied to the mixture, and one or more RF magnetic pulses are also applied to the mixture. Multiple assays may be conducted simultaneously through the use of magnetic resonance imaging techniques.

43 Claims, 11 Drawing Sheets

METHODS FOR HIGH THROUGHPUT CHEMICAL SCREENING USING MAGNETIC RESONANCE IMAGING

BACKGROUND OF THE INVENTION

This invention relates generally to the field of chemical screening, and in particular to the screening of various chemicals for biological or other activity. More specifically, the invention relates to assays where nuclear magnetic resonance is employed as a screening tool.

Modern chemistry has proven to be effective in creating a wide assortment of chemicals that may be useful for a variety of applications including drug therapy, industrial manufacturing, painting, and the like. A recent development in the field of modern chemistry is that of combinatory chemistry where vast libraries of chemical compounds may rapidly be created. For example, combinatorial chemistry techniques are described in U.S. Pat. No. 5,503,805, the complete disclosure of which is herein incorporated by reference.

One significant challenge for the modern chemist is the ability to find useful applications for the vast libraries of chemicals now being created. For example, the drug discovery industry is currently expending significant resources to identify chemicals that may be used as drugs to treat a wide variety of ailments. In order to determine whether a chemical will be useful for a particular application, the chemical needs to be tested in a particular environment to determine if the chemical is active under certain conditions, often referred to as screening. This can be particularly challenging if the number of chemicals to be screened is large. For example, Wilhelm Stahl, "What is the Future of High Throughput Screening?" *Journal of Biomolecular Screening,* Volume 4, Number 3, pp. 117–118, 1999; Anthony M. Maffia III et. al, "Miniaturization of a Mammalian Cell-Based Assay: Luciferase Reporter Gene Readout in a 3 Microliter 1536-Well Plate", *Journal of Biomolecular Screening,* Volume 4, Number 3, pp. 137–142, 1999; and Laura Abriola et al., "Digital Imaging as a Detection Method for a Fluorescent Protease Assay in 96-Well and Miniaturized Assay Plate Formats", *Journal of Biomolecular Screening,* Volume 4, Number 3, pp. 121–127, 1999, the complete disclosures of which are herein incorporated by reference, describe the challenges associated with the demand to increase high throughput screening.

Various types of assays have been developed to screen chemicals for activity at the cellular level. For example, some assays that have been utilized include cell reporter assays, such as lawn assays, direct binding assays, and the like. Further, various types of chemical handling devices and automated equipment have been developed to increase the throughput or efficiency of the screening process. For example, many assays utilize multiwell plates, such as standard 96 well plates where 96 chemicals may be screened in parallel. Other equipment used to facilitate such assays includes robots for plate and chemical handling, plate readers employing CCD cameras, and the like. Merely by way of example, useful apparatus and equipment are described in U.S. Pat. No. 5,722,470 and in copending U.S. patent application Ser. No. 08/834,803, filed Apr. 3, 1997, the complete disclosures of which are herein incorporated by reference.

Even so, there is still a need for other techniques to screen for biological or other activity in a high throughput manner, particularly in view of the large chemical libraries now being created. Further, a need also exists for new assays and associated screening techniques that may be used to screen chemicals for certain types of activity. Hence, the invention is related to alternative assays and screening techniques that are particularly adapted for high throughput screening and/or for providing alternative avenues to screen for certain types of activity.

SUMMARY OF THE INVENTION

The invention utilizes nuclear magnetic resonance to evaluate a wide variety of assays. In one embodiment, a screening method is provided where an assay is performed where one or more chemicals and/or entities are present in a mixture to produce an outcome. A static magnetic field $B_0$ is applied to the mixture along with one or more RF magnetic pulses. Resulting FID or echo signals are measured and evaluated to evaluate the outcome of the assay. In this way, nuclear magnetic resonance may be employed to evaluate the outcome of a wide variety of assays.

In one aspect, the assay is performed in a plate having a plurality of wells. The mixture in each well includes a different chemical and/or entity, and spatially dependent $B_0$ gradient fields are applied to the wells. FID or echo signals are then measured and evaluated from each of the wells. In this way, multiple outcomes may be evaluated using nuclear magnetic resonance in a high throughput manner. Optionally, the wells may be arranged in a three-dimensional array to increase the throughput of the screening procedure. For example, multiple plates may be stacked on top of each other and then screened using nuclear magnetic resonance.

In another aspect, the entities in the mixture may comprise cells which each produce a different test product. Each test product may produce a detectable nuclear magnetic resonance signal that is dependent on the degree of interaction of the test compound with the mixture. For example, the cells may produce a test product with a chemical shift that is different from that of water protons. In another aspect, the assay proceeds by providing the mixture with a test compound that causes a detectable nuclear magnetic resonance signal to be produced to indicate whether the test compound is biologically active in the mixture.

In one particular aspect, a test compound may be combined with at least one cell in an aqueous medium. Biological activity of the test compound is indicated when the test compound binds to a receptor on the cell surface or within the cell. In so doing, an enzyme is produced that either directly or indirectly affects the relaxation properties of water protons to indicate that the test compound is biologically active. For example, the enzyme may modify the relaxation properties of water protons by cleaving a probe molecule in the mixture. In this way, the exposure of a paramagnetic atom in the probe molecule to water protons may be increased to thereby decrease the T1 relaxation rate of the water protons. As one specific example, the enzyme may comprise beta-galactosidiase, and the probe molecule may comprise a chelated gadolinium atom that is complexed with a galactose molecule. In this manner, the galactosidiase will cause the galactose molecule to be cleaved from the chelated gadolinium.

In another aspect of the method, a test compound may be provided in an aqueous medium and mixed with a chemical or entity that when reacting with the test compound changes the pH of the medium. The change in pH is measurable using nuclear magnetic resonance to indicate that the test compound is biologically active. For example, the change in pH of the medium may cause a change to the ionization of polymer molecules that are also in the medium. As a result, the viscosity of the medium is changed, thereby affecting nuclear magnetic resonance relaxation properties, spin density and/or the diffusion coefficient of the water protons of the aqueous medium. As another example, the change in pH of the medium may cause a change to the configuration of gel particles that are included within the medium. The configuration change of the gel particles affects nuclear magnetic resonance relaxation properties, spin density and/or the diffusion coefficient of the water protons of the medium. In one aspect, the medium may include a pH sensitive contrast agent that causes the nuclear magnetic resonance relaxation properties of water protons or other nuclei of the medium to be changed in a manner that is reflective of pH. In this way, a change in pH affects the contrast agent that in turn affects the nuclear magnetic resonance relaxation properties of water protons or other nuclei. pH sensitive contrast agents may contain lanthanide metals including Ce, Pr, Nd, Sm, Eu, Gd, Db, Dy, Ho, Er, Tm, or Yb, or other paramagnetic elements, such as Fe, Mn, or $^{17}O$. One exemplary contrast agent that may be utilized is Fe(III)meso-tetra(4-sulfonatophenyl)porphine (Fe-TPPS4). Another exemplary contrast agent comprises $H_2^{17}O$.

In still another aspect, the mixture may include an aqueous medium that includes a shift reagent that affects the chemical shift properties of the water protons or other nuclei of the aqueous medium in a manner that is reflective of pH. Hence, a change in pH will affect the shift reagent that in turn will affect the chemical shift properties of the water protons or other nuclei to permit the outcome of the assay to be evaluated using nuclear magnetic resonance. As one example, the shift reagent may contain a lanthanide metal such as Ce, Pr, Nd, Sm, Eu, Gd, Db, Dy, Ho, Er, Tm, or Yb or another paramagnetic element. Examples of shift reagents that may be utilized include $Tm(DOTP)^{5-}$, the thulium (III) complex of 1,4,7,10-tetraazacylododecane-N,N',N'',N'''-tetra(methylenephospate). $Dy(PPP)_2^{7-}$-dysprosium tripolyphosphate, and the like.

In yet another aspect of the method, the test compound may be placed into an aqueous medium, with the chemical and/or entity being selected such that, when reacting with the test compound, the temperature of the medium changes. In this manner, the change in temperature may be measured using nuclear magnetic resonance to indicate that the test compound is biologically active. For example, the change of temperature may be reflected by a change in the nuclear magnetic resonance relaxation rates, magnetization transfer properties, diffusion constant or spin density of the water protons. As another example, the change in temperature may be reflected by a change in the chemical shift of water protons or other nuclei of the aqueous medium. Conveniently, the aqueous medium may include a contrast agent that affects the chemical shift properties of the water protons or other nuclei in a manner that is reflective of temperature. Examples of contrast agents that may be utilized include those containing a lanthanide metal such as Ce, Pr, Nd, Sm, Eu, Gd, Db, Dy, Ho, Er, Tm, or Yb. One exemplary contrast agent that may be utilized comprises Pr[M0E-D03A].

In another particular aspect, the assay utilizes a cell disposed in an aqueous medium. The cell is configured to produce a test product that has a chemical shift different from that of water protons to indicate that the compound is biologically active. Examples of test products that may be produced having such a chemical shift include choline, lactate, N-acetyl-aspartate, N-acetyl-glutamate, ATP, ADP, alanine, creatine, phosphol-creatine, phospho-choline, citrate, myo-inositol, methanol, ethanol, and the like.

In still another aspect, the mixture may include an aqueous medium where a test compound is combined with a cell that when reacting with a test compound causes the concentration of one or more intra-cellular ions to change in a manner that is detectable by nuclear magnetic resonance. Examples of intracellular ions that may be used include $^{23}Na$, $^{7}Li$, $^{25}Mg$, $^{39}K$, $^{43}Ca$, $^{87}Rb$, $^{113}Cd$, and the like. In an alternative aspect, the mixture may include one or more cells in an aqueous medium, with the aqueous medium containing a shift reagent that allows for the separation of extracellular and intracellular ions by their different chemical shifts. Examples of shift reagents that may be used to allow for such separation include lanthanide metals, such as Ce, Pr, Nd, Sm, Eu, Gd, Db, Dy, Ho, Er, Tm, and Yb. Exemplary shift reagents that may be utilized include $Dy(PPP)_2^{7-}$-dysprosium tripolyphosphate, $Tm(DOTP)^{5-}$, the thulium (III) complex of 1,4,7,10-tetraazacylododecane-N,N',N'',N'''-tetra(methylenephospate), $Dy(DPA)_3^{3-}$-dysprosium dipicolinate pyridine-2,6-dicarboxylate, $Dy(NTA)_2^{3-}$, dysprosium nitrilotriacetate, $Dy(TTHA)^{3-}$-dysprosium triethylenetetraminehexaacetate, $Tm(PPP)_2^{7-}$, and $Tm(TTHA)^{3-}$. Conveniently, the extra-cellular and intracellular ions may be differentiated by their T2 relaxation properties. Alternatively, the extra cellular and intracellular ions may be differentiated by the use of a multiple quantum filter. In another alternative aspect, the extra cellular ions may be washed out of the aqueous medium before nuclear magnetic resonance measurements are made.

In still another aspect, the mixture may include an aqueous medium comprising water protons. A contrast agent is introduced into the aqueous medium that changes conformation upon binding to an ion in the mixture. In this way, the relaxation properties of the water protons are changed and may be measured using nuclear magnetic resonance. Examples of contrast agents that may be utilized include those containing a lanthanide metal, such as Ce, Pr, Nd, Sm, Eu, Gd, Db, Dy, Ho, Er, Tm, or Yb, or other paramagnetic element, such as Fe or Mn. One exemplary contrast agent that may be utilized comprises DOPTA-Gd.

In another embodiment, the invention provides a screening method where a plurality of plates are provided that each include multiple wells or sample chambers. A chemical and/entity is introduced into at least some of the wells of each plate. A test compound is also introduced into the wells containing the chemical and/or entity. The plates may then be stacked on top of each other and inserted into a nuclear magnetic resonance device. Such a device is then employed to screen for any biologically active test compounds.

The invention further provides an exemplary multi-well plate that comprises a plate body having a plurality of wells or sample chambers. At least one RF coil is disposed within the plate body. Further, a connector is provided to permit the RF coil to be coupled to a magnetic resonance imaging system. In this way, the RF coil is provided within the plate body so that a separate RF coil is not needed in the magnetic resonance imaging system.

In still a further embodiment, a multi-well plate is provided having a plate body with a plurality of wells or sample chambers. Further, the plate body is constructed of a material with desirable magnetic susceptibility properties to minimize spatial distortions and signal losses. Use of such a material is advantageous in that it facilitates detection of FID or echo signals when screening the plates using nuclear magnetic resonance. Examples of materials that may be used include polystyrene, polycarbonate and polypropylene.

In an alternative embodiment, a multiwell plate system may be constructed to facilitate its use within a magnetic resonance imaging device. For example, the multi-well plate system may include a plurality of plates that are stacked on top of each other, with a generally spherical or cylindrical body disposed about the plates. Alternatively, the plates may be configured so that they form a generally spherical or cylindrical body when stacked on top of each other.

In yet another embodiment, the invention provides a multi-well plate system that comprises a plate body having a plurality of sample chambers. Each sample chamber has an associated fluid entrance port and a vent. In this way, test mixtures may be introduced into the sample chambers through the entrance ports. A plugging apparatus is provided to plug the fluid entrance ports and the vents after the test mixtures have been introduced into the plate body. In this way, the sample chambers will be essentially void of any air or other gas bubbles to facilitate measurements taken utilizing nuclear magnetic resonance. Conveniently, the fluid entrance ports in the vents may be arranged to permit multiple plates to be stacked on top of each other and filled with test mixtures.

DESCRIPTION OF THE SPECIFIC EMBODIMENTS

As used herein, the following terms are defined as follows:

Test Compound—A chemical that is to be evaluated for activity by an assay. A non-limiting example is a molecule from a combinatorial chemical library that is to be tested for binding activity to a cell surface receptor.

Test Product—A chemical that is produced by an assay. One non-limiting example is a reporter enzyme such as beta-galactosidase that is produced by an engineered cell line. As another non-limiting example, an assay may have several test products. A cell may be engineered to produce N-acetyl transferase which catalyzes the formation of N-acetyl-aspartate from acetyl coA and L-aspartate. In this specific case, both N-acetyl transferase and N-acetyl-aspartate are test products.

Entity—An object that is added to a mixture and required for an assay. Entities may include but not be limited to cells, viruses, phage, bacteria, plants, beads, solid supports or parts thereof.

Probe Molecule—A molecule that translates an assay result into a NMR detectable signal. For example, a probe molecule may comprise a chelated gadolinium atom complexed with a galactose molecule. In the presence of a test product, such as beta-galactosidase, the galactose molecule is cleaved from the chelated gadolinium thereby decreasing the T1 of water molecules in the medium.

Mixture—An aqueous solution containing test compounds, test products, entities and/or probe molecules required for or produced by the assay.

The invention utilizes the principles of nuclear magnetic resonance (NMR) to evaluate the outcome of a wide variety of assays. As such, the invention provides useful techniques to screen various chemicals for biological or other activity. According to the invention, NMR is used to generate an image of a plate having multiple wells or test chambers, thus allowing for localization of activity to specific wells or chambers. Spatial localization of NMR sensitive nuclei is known as magnetic resonance imaging (MRI). Because of the nature of MRI, a three-dimensional array of wells or test chambers may conveniently be imaged. For example, plates having multiple wells may be stacked on top of each other and then imaged using MRI. Often, the time required to image a single plate may be equivalent to the time required to image multiple plates. In this way, the throughput of the screening process is significantly increased as compared to typical optical imaging techniques that provide only a two-dimensional readout. Another particular advantage of using NMR is that it provides alternative ways to evaluate the outcome of assays, thereby offering information not available using traditional screening techniques.

The assays of the invention may involve the use of one or more chemicals and/or entities that produce an outcome that is evaluated using NMR. Advantageously, the invention may utilize a wide variety of chemicals and/or entities, making the invention a highly versatile screening tool. For example, the assay may involve the use of different test chemicals that are screened in parallel. Such high throughput screening may be particularly useful with today's large combinatorial chemistry libraries which include vast numbers of different chemical compounds that need to be screened for activity. Hence, with the invention. NMR may be employed to determine whether test chemicals are biologically active in a high throughput manner. As an example, the entity may comprise a cell that produces a test product such as a protein or enzyme that is detectable either directly or indirectly via NMR.

The invention may utilize NMR in a variety of ways to localize wells or test chambers to determine if a chemical or chemical compound is active. For example, assays may be developed where a certain outcome may be measured and evaluated using NMR if the outcome of the assay gives a positive result, e.g., when the chemical is active. Merely by way of example, the invention may utilize cell-based reporter assays to determine biological or other activity. For example, the assay may be configured to enzymatically induce T1 or T2 changes of water protons in an aqueous medium if a test compound is active. For instance, a cell may be engineered so that when a test compound actively binds to a cell surface receptor, an enzyme is produced that either directly or indirectly affects the relaxation properties of neighboring water protons. The T1 and T2 changes may be measured using NMR and may be used as a basis for contrast in the assay.

The invention provides other assays (that may or may not be cell-based reporter systems) that are configured to affect T1 or T2 water relaxation rates or other NMR sensitive parameters. For example, the assays may take place in an aqueous medium, with the assays being configured to affect the diffusion coefficient, magnetization transfer properties, spin density, and/or chemical shift of the water protons of the aqueous medium. For example, assays may be configured such that biological or other activity changes the viscosity of the aqueous medium, thereby affecting the relaxation properties of the water protons in a measurable manner. A change in viscosity may also affect the diffusion coefficient of water protons in the aqueous medium. Such a change in the diffusion coefficient may be detected by NMR and serve as a basis for contrast in the assay.

Another example of a NMR sensitive parameter is pH. Small changes in pH may have a significant effect on an equilibrium volume and configuration of certain gels. As the configuration of such gels changes, the T1 and T2 relaxation rates or diffusion coefficient of water protons of the gels may be affected. Still another NMR sensitive parameter is a change of temperature. Hence, assays may be provided where the temperature of the medium changes when activity occurs and may be detected using NMR. For example, the temperature-dependent chemical shift of water may be detected using NMR. As another example, a temperature sensitive contrast agent may be provided that affects relaxation properties of water protons.

The invention further provides various other cell-based reporter systems to screen for activity. For example, NMR may be used to measure specific metabolite concentrations, e.g., choline, creatine, and the like using chemical shift imaging techniques. Hence, a cell reporter system may be configured to produce a molecule having a different chemical shift than water. In this way, detection of the produced molecule is direct. The invention also provides for testing of other cell-based systems that are not reporter assays. For example, the goal of the assay may be to quantify the amount of test product being produced independently of cellular activation by a test compound.

Other cell-based systems may be utilized that rely on the detection of NMR-sensitive nuclei other than protons. For example, one such assay is a 23-Na ion channel assay that involves the measurement of intracellular sodium concentrations after application of a test compound. The assay uses the shift reagent dysoprosium to allow for separation of intracellular and extracellular ion pools using 23-Na NMR spectroscopy. Conveniently, such an assay may be conducted in a single test tube or in a multi-well assay format suitable for NMR. Other techniques for differentiating the extra-cellular and intra-cellular ions include T2 relaxation measurements and the use of a multiple quantum filter. Other cell-based assays may utilize a contrast agent that changes confirmation upon binding to an ion of the cell to change the relaxation properties of the water protons.

The invention further provides a variety of equipment and systems that may be utilized to facilitate the screening of chemicals using NMR. For example, the invention provides a variety of plates that include multiple wells or test chambers to facilitate high throughput screening. For instance, the wells may be configured in a three-dimensional format to increase throughput. The plates may also be configured to minimize the magnetic susceptibility effects to reduce $B_0$ field inhomogeneities. For example, the shape of the plates may be configured to reduce such susceptibility effects. Further, the material with which the plates are constructed may be configured to reduce $B_0$ field inhomogeneities. Still further, the plates may be configured so that when the test chemicals or compounds are introduced into the wells or test chambers, substantially all air is removed. In still another alternative, one or more RF coils may be incorporated into the plates themselves, thereby increasing sensitivity and reducing costs.

As previously described, the invention employs the use of NMR to screen a wide variety of chemicals. As it is known in the art, NMR involves the detection of nuclear magnetic moments with specific spin precession frequencies that are proportional to the local magnetic field. The radio frequency (RF) signals resulting from the precession of the spins are received using pickup coils. More specifically, when matter is placed within a static magnetic field, the nuclear magnetic moments in the matter tend to orient themselves parallel to the field. This leads to a paramagnetic polarization in the direction of the magnetic field, often referred to as the Z direction. The static magnetic field in the Z direction is often represented by the reference symbol $B_0$. When an oscillating magnetic field (B1) with frequency at or near the resonance condition is applied in the X or Y direction, the polarization vector is deflected from the Z direction while also rotating about the Z-axis. Such a resonance condition is represented by $|\omega=B_0\gamma|$, where $B_0$ is the amplitude of the applied static magnetic field, $\omega$ is the nuclear precession frequency, and $\gamma$ is the gyromagnetic ratio. The gyromagnetic ratio is constant for a given isotope. After rotation of the magnetic polarization vector from the Z-axis, the oscillating magnetic field B1 may be turned off. The spins will continue to process about the Z-axis causing a voltage or electromotive force (EMF) to be induced in a detector or pickup coil that is aligned perpendicular to the X-Y plane. Such a signal is referred to as a NMR signal.

Various NMR sensitive parameters may be employed to visualize contrast in the matter. One such parameter is nuclear magnetic relaxation, which is described by the T1 and T2 relaxation time constants. The nuclear magnetic relaxation is the rate of return of the spin system to equilibrium. T1 represents the time constant for the return of the longitudinal magnetization, while T2 represents the transverse relaxation time. A general discussion of NMR, including relaxation rates, is found in Felix Wehrli, "The Origins and Future of Nuclear Magnetic Resonance Imaging," *Physics Today*, pages 34–42, June 1992, the complete disclosure of which is herein incorporated by reference. Another NMR sensitive parameter is chemical shift where the resonance frequency of a given nucleus is also dependent upon its molecular environment (i.e. the chemical structure of the molecule that the nucleus is a part of). This allows for measurement of concentrations of several different molecules simultaneously.

Figure 1:
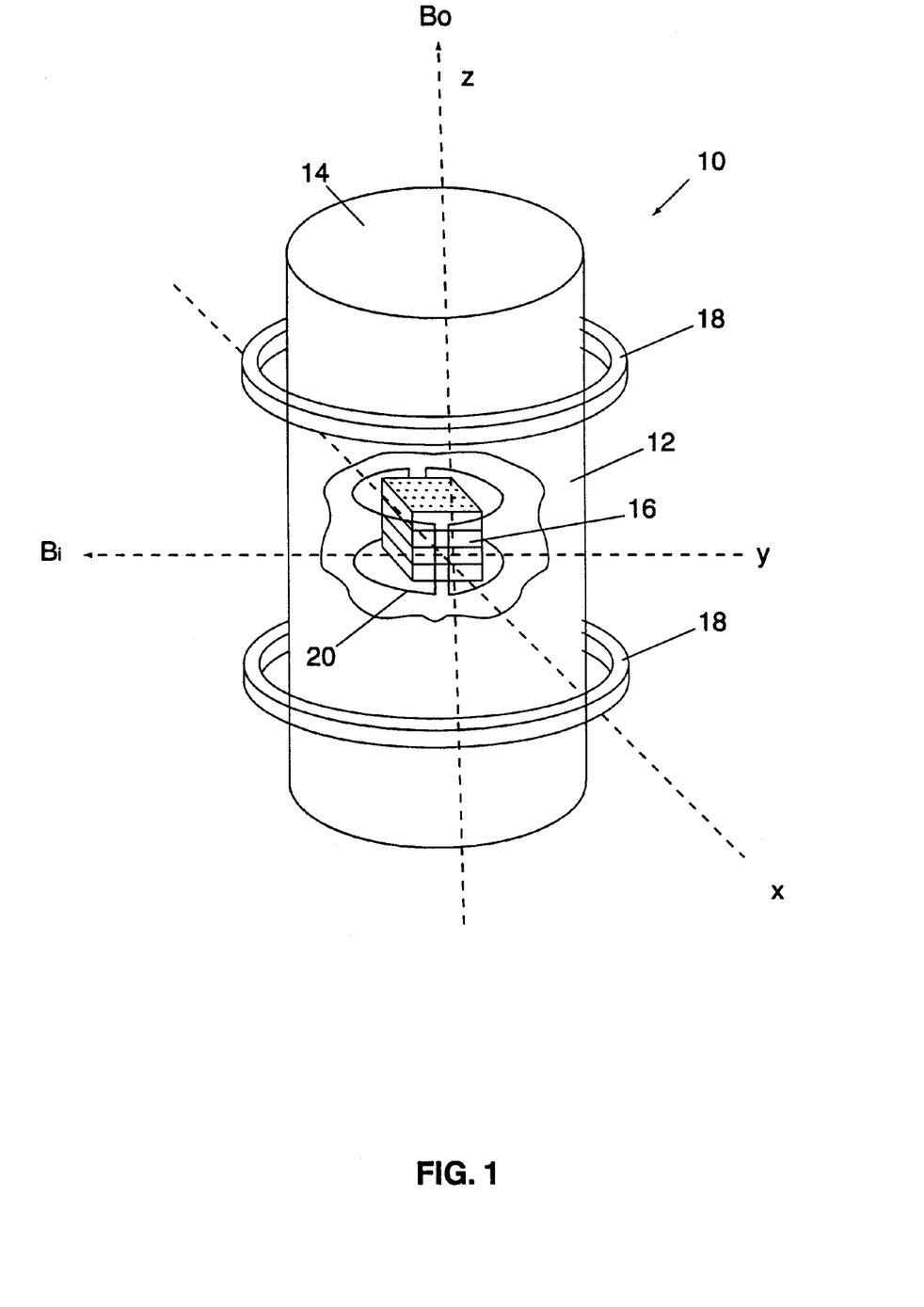
FIG. 1 is a schematic illustration of one embodiment of a nuclear magnetic resonance device that may be employed to screen chemicals according to the invention.

Referring now to FIG. 1, an embodiment of a coil apparatus 10 of an NMR imaging system will be described. Coil apparatus 10 comprises a cylindrical body 12 that defines a chamber 14. Disposed within chamber 14 are a plurality of multi-well plates 16 that are to be imaged with the imaging system. As shown, a Z axis extends through a longitudinal axis of cylindrical body 12. The X and Y axes lie in a plane perpendicular to the Z axis.

Coil apparatus 10 further includes a pair of coils 18 that form a magnet that is employed to generate a uniform static magnetic field $B_0$ in the direction of the Z axis. Although not shown, a complex gradient coil is preferably wound on cylindrical body 12 to create a gradient-field $G_x$. Coil apparatus 10 further includes a saddle or detection coil 20 that is positioned about plates 16. Saddle coil 20 is employed to create a RF field $B_1$. Conveniently, detection coil 20 may be employed to detect FID or echo signals that are used by the imaging system to produce an image of plate 16. Plates 16 are configured so that the Z axis extends vertically upward through plates 16. A general discussion of other types of coil apparatus and associated imaging systems are described in U.S. Pat. Nos. 5,652,516, 4,999,580, 5,653,233 and in W. V. House, "IEEE Transactions On Nuclear Science", Vol. NS-27, pp. 1220–1226 (June 1980), Pykett, NMR Imaging in Medicine, *Scientific American,* May 1982, pp. 78–88; Paul J. Keller, "Basic Principles of Magnetic Resonance Imaging," GE Medical Systems (1991), the complete disclosures of which are herein incorporated by reference.

Hence, with coil apparatus 10, a strong static magnetic field $B_0$ is generated by coils 18 to line up atoms whose nuclei have an odd number of protons and/or neurons, i.e., atoms whose nuclei have spin angular momentum and a magnetic dipole moment. Saddle coil 20 is employed to generate a second RF earth magnetic field $B_1$, applied as a single pulse transverse to $B_0$. This causes the nuclei to be flipped, such as for example, by 90 or 180 degrees. After excitation, the nuclei in the wells of plates 16 gradually return to alignment with the static field and give Lip the energy in the form of weak but detectable free induction decay (FID) or echo signals. Such detected signals may then be utilized by a computer to produce images.

As previously mentioned, the excitation frequency and the FID frequency are defined by the Larmor relationship where the angular frequency, $\omega_0$, of the precession of the nuclei is the product of the magnetic field, $B_0$ and the magneto gyric ratio, $\gamma$, which is a physical constant for each nuclear species. Hence, by superimposing a linear gradient field, $B_Z = Z \cdot G_Z$ on the static unform field, $B_0$, which defines the Z axis nuclei in a selected XY plane in plate 16 may be excited by proper choice of the frequency spectrum of the transverse excitation field applied along the X and Y axes. Similarly, a gradient field may be applied in the XY plane during detection of the FID or echo signals to spatially localize the FID or echo signals in the plane. The angle of nuclei spin flip in response to a RF pulse excitation is proportional to the integral of the pulse over time.

Figure 2:
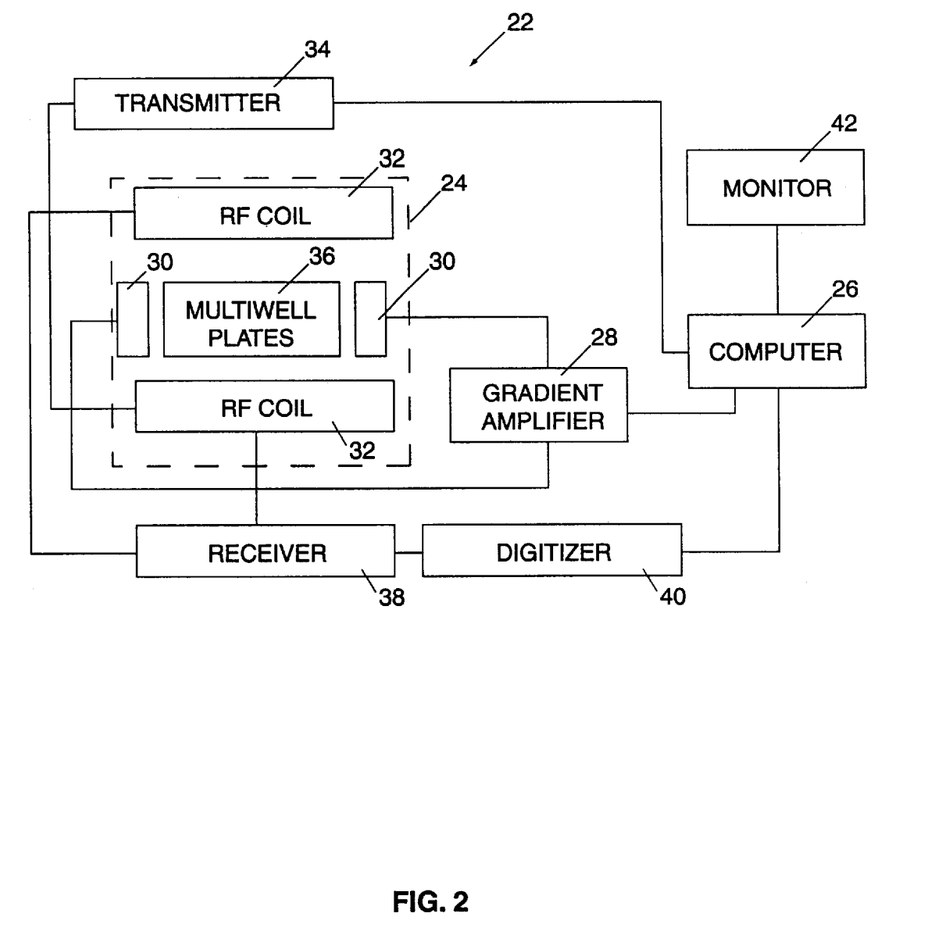
FIG. 2 is a schematic block diagram of a nuclear magnetic resonance system that may be employed to screen chemicals according to the invention.

Referring now to FIG. 2, a schematic block diagram of an imaging system 22 will be described. Imaging system 22 includes a magnet 24 that is employed to produce a uniform static magnetic field $B_0$. System 22 further includes a computer 26. Coupled to computer 26 is a gradient amplifier 28 that in turn is coupled to gradient coils 30. In this way, a gradient field may be energized by gradient amplifier 28 and gradient coils 30. RF coils 32 are further included to impress a RF magnetic moment at the Laramore frequency. This is controlled by a transmitter 34 that is also coupled to computer 26. After the selected nuclei within multi-well plates 36 have been flipped, RF coils 32 are employed to detect the FID or echo signals, which is passed through a receiver 38 and then through a digitizer 40 for processing by computer 26. Conveniently, a monitor 42 may be coupled to computer 26 to display an image of multi-well plates 36.

Figure 3:
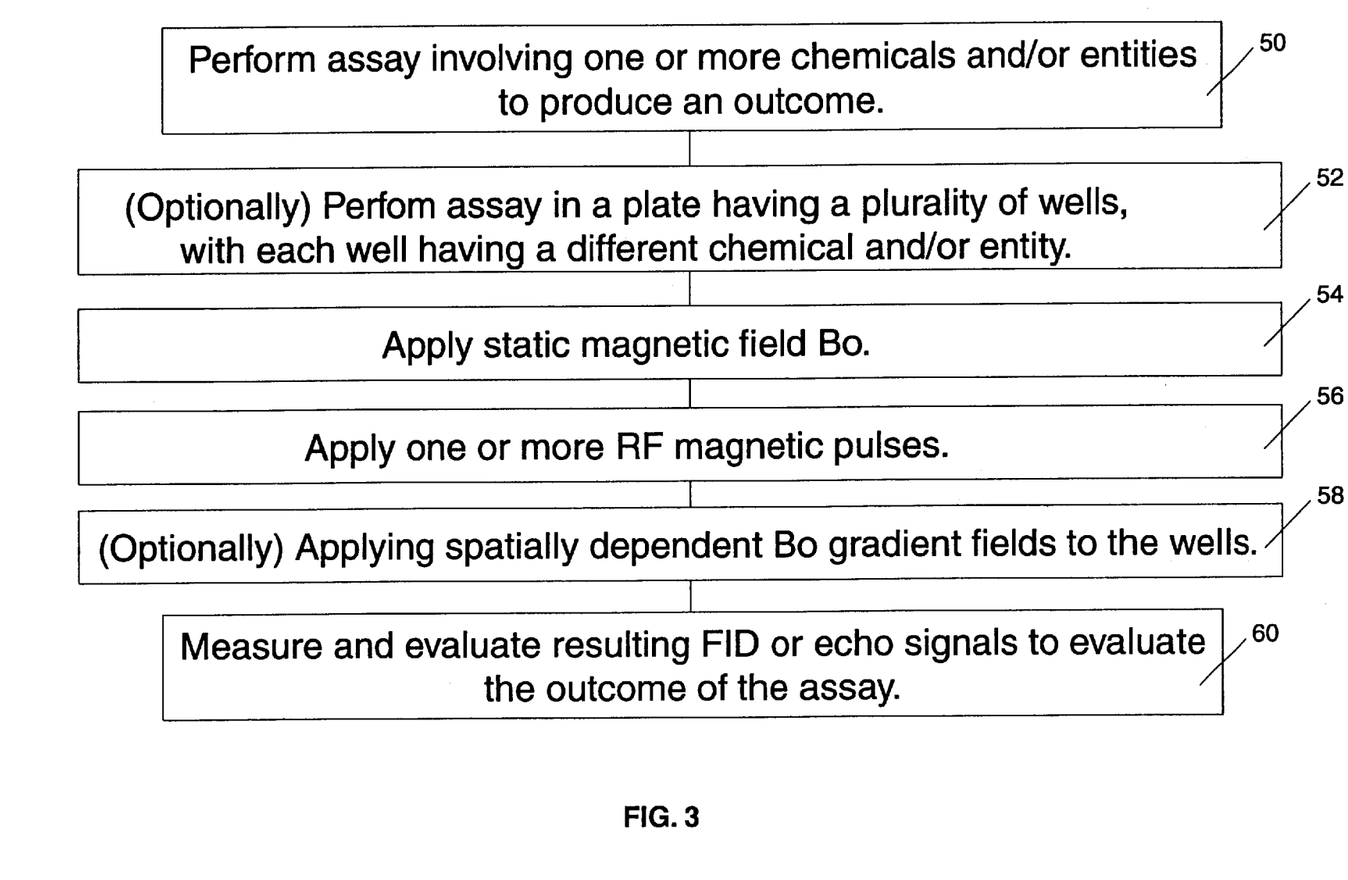
FIG. 3 is a flow chart illustrating one method for screening chemicals according to the invention.

Referring now to FIG. 3, one method that may be employed to screen chemicals for activity will be described. As shown in step 50, the method proceeds by performing an assay that involves one or more chemicals and/or entities that are present in a mixture to produce an outcome. Conveniently, the assay may be performed in a plate having a plurality of wells or test chambers, with each well having a different chemical and/or entity as shown in step 52. A static magnetic field $B_0$ is applied to the mixture along with one or more RF magnetic pulses as shown in steps 54 and 56. Typically, spatially dependent $B_0$ gradient fields are also applied to the wells as shown in step 58. Resulting FID or echo signals are measured and evaluated to evaluate the outcome of the assay as shown in step 60.

Figure 4:
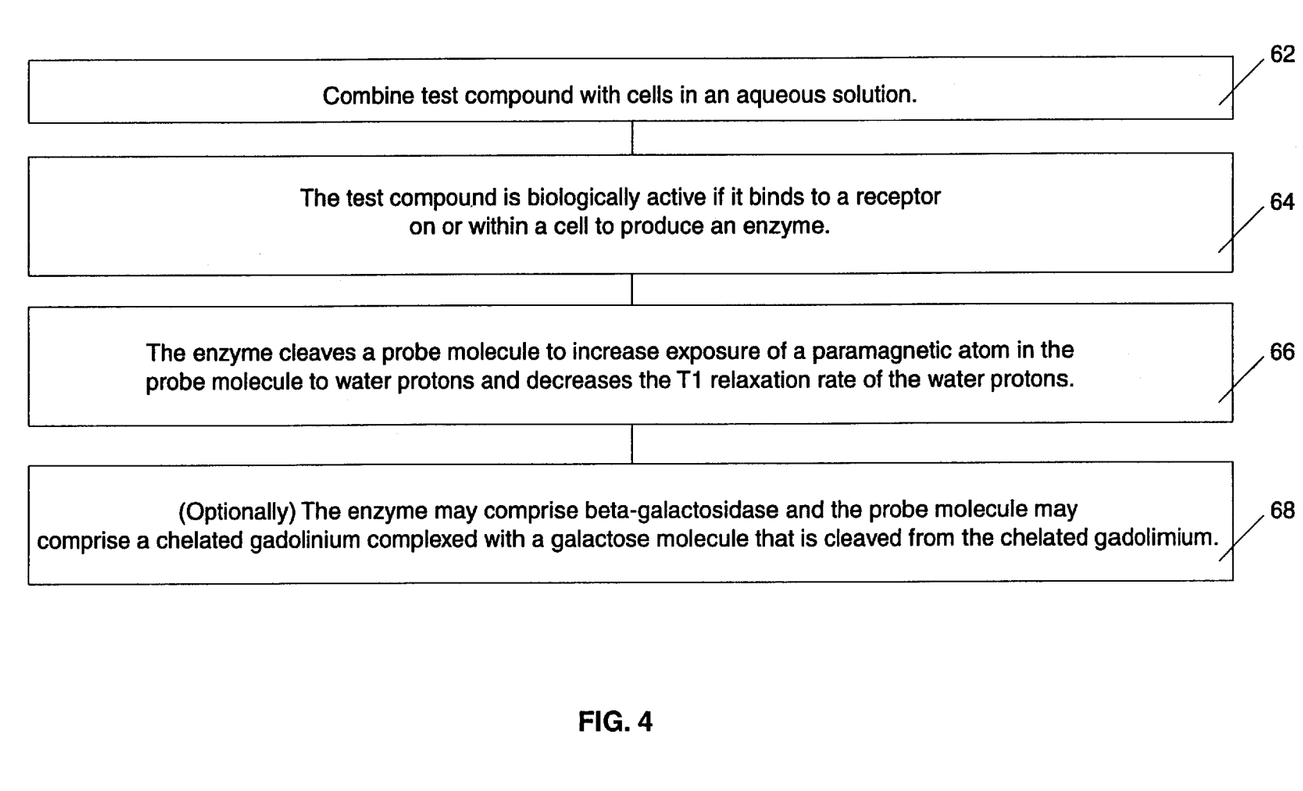
FIG. 4 is a flow chart illustrating a cell reporter assay useful when screening with nuclear magnetic resonance according to the invention.

As illustrated in step 62 of FIG. 4, the assay may involve the combination of a test compound with cells in an aqueous mixture or solution. As shown in step 64, the test compound is biologically active if it binds to a receptor on or within a cell to produce an enzyme. In turn, the enzyme cleaves a probe molecule to increase exposure of a paramagnetic atom in the probe molecule to water protons, thereby decreasing the T1 relaxation rate of the water protons as shown in step 66. As shown in step 68, the enzyme may comprise beta-galactosidase, and the probe molecule may comprise a chelated gadolinium atom that is complexed with a galactose molecule that is cleaved from the chelated gadolinium. In the presence of beta-galactosidase, i.e., the reporter enzyme, the sugar molecule is cleaved. This exposes the gadolinium atom to neighboring water molecules and decreases the T1 relation rate of the surrounding water protons.

Hence, one configuration of the assay may be to mix the cells in the wells of a plate with a test compound, typically having a different test compound in each well. After allowing for sufficient reaction time, the cells may be lysed and a chelated gadolinium compound added to each of the wells. Any activated cells produce beta-galactosidase which then reacts with the substrate. The plates may then be placed in a NMR machine and imaged. The T1 measurements of the water protons may be used to localize wells that contain active compounds. One particular chelated gadolinium compound that may be employed is described in Moats, et al., A "Smart" Magnetic Resonance Imaging Alert That Reports on Specific Enzymatic Activity, *Angew. Chem. Int. ED. Engl.* 1997, 36, No. 7, the complete disclosure of which is herein incorporated by reference.

Figure 5:
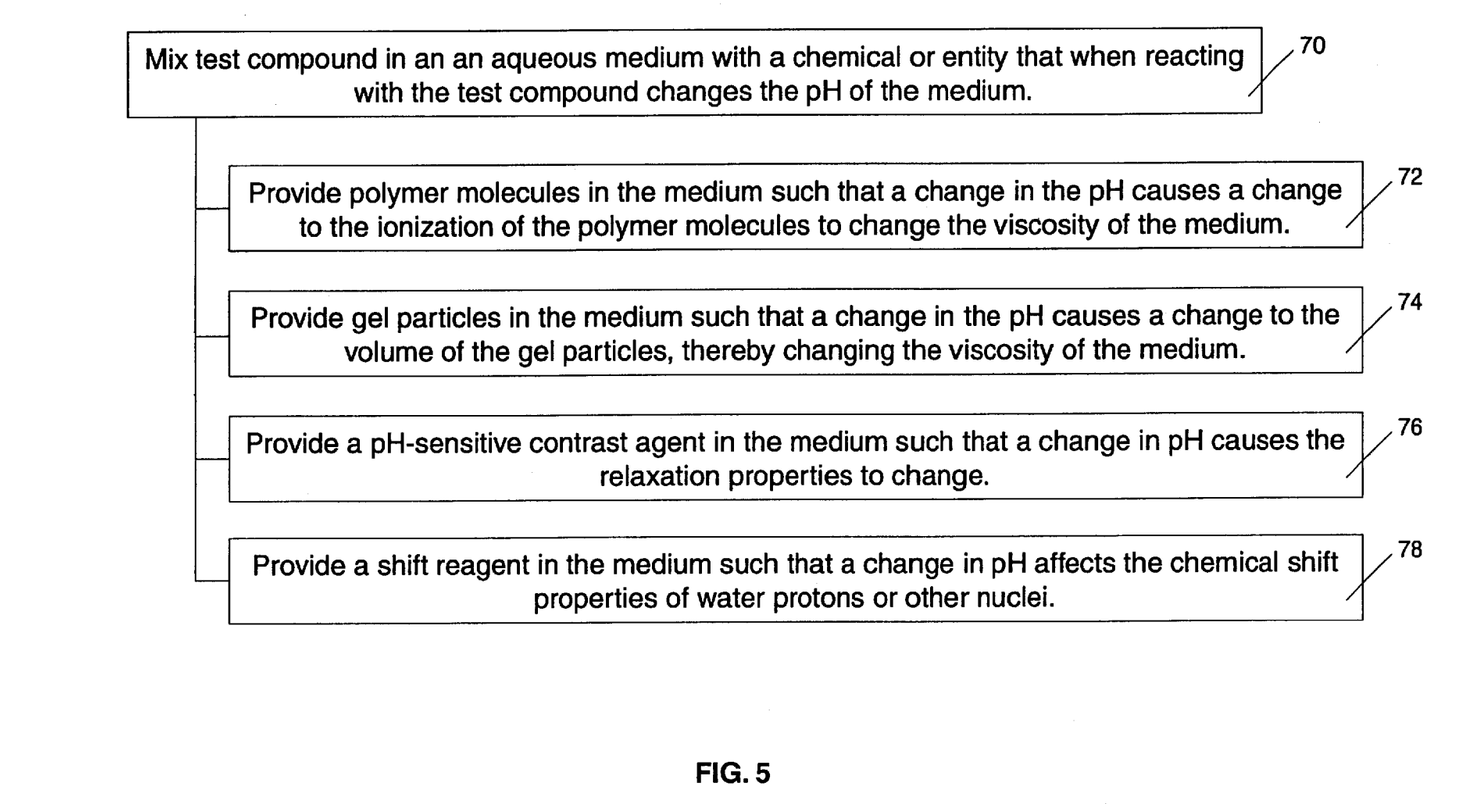
FIG. 5 is a diagram illustrating various assays where a reaction by a test compound changes the pH of an aqueous medium, with the change of pH being detectable using nuclear magnetic resonance according to the invention.

As shown in FIG. 5, the invention may utilize assays where a test compound is mixed in an aqueous medium with a chemical or entity that, when reacting with the test compound, changes the pH of the aqueous medium. The change in pH may then be measured using nuclear magnetic resonance to indicate that the test compound is biologically active (see step 70). One example of how such an assay may be configured is illustrated in step 72 where polymer molecules are included in the aqueous medium so that a change in the pH causes a change to the ionization of the polymer molecules. In turn, this changes the viscosity of the aqueous medium, thus affecting nuclear magnetic resonance relation properties, spin density and/or the diffusion coefficient of the water protons. The change in such properties may then be detected using nuclear magnetic resonance to determine biological activity.

As shown in step 74, an alternative assay utilizes gel particles in the aqueous medium. In this way, a change in the pH causes a change to the volume or configuration of the gel particles, thereby affecting nuclear magnetic resonance relaxation properties, spin density and/or the diffusion coefficient of the water protons in the mixture.

In step 76, the assay utilizes a pH sensitive contrast agent in the aqueous medium. In this way, a change in pH causes the nuclear magnetic resonance relaxation properties of water protons or other nuclei in the aqueous medium to be changed in a manner that is reflective of pH. Examples of contrast agents that may be utilized include those agents that contain a lanthanide metal, such as Ce, Pr, Nd, Sm, Eu, Gd, Db, Dy, Ho, Er, Tm, Yb, and the like, or another paramagnetic element, such as Fe, Mn, $^{17}O$, or the like. Specific contrast agents that may be utilized include $H_2^{17}O$ and Fe(III)meso-tetra(4-sulfonatophenyl)porphine (Fe-TPPS4).

As another alternative, a shift reagent may be provided in the aqueous medium as shown in step 78. The shift reagent is configured such that a change in pH affects the chemical shift properties of the water protons or other nuclei in a manner that is reflective of pH. The change in chemical shift properties may then be measured using nuclear magnetic resonance to determine whether the test compound is biologically active. Examples of shift reagents that may be used include those containing a lanthanide metal, such as Ce, Pr, Nd, Sm, Eu, Gd, Db, Dy, Ho, Er, Tm, or Yb, or another paramagnetic element. Examples of specific shift reagents that may be utilized include $Tm(DOTP)^{5-}$, the thulium (III) complex of 1,4,7,10-tetraazacylododecane-N,N',N'',N'''-tetra(methylenephospate). $Dy(PPP)_2^{7-}$-dysprosium tripolyphosphate, and the like.

Figure 6:
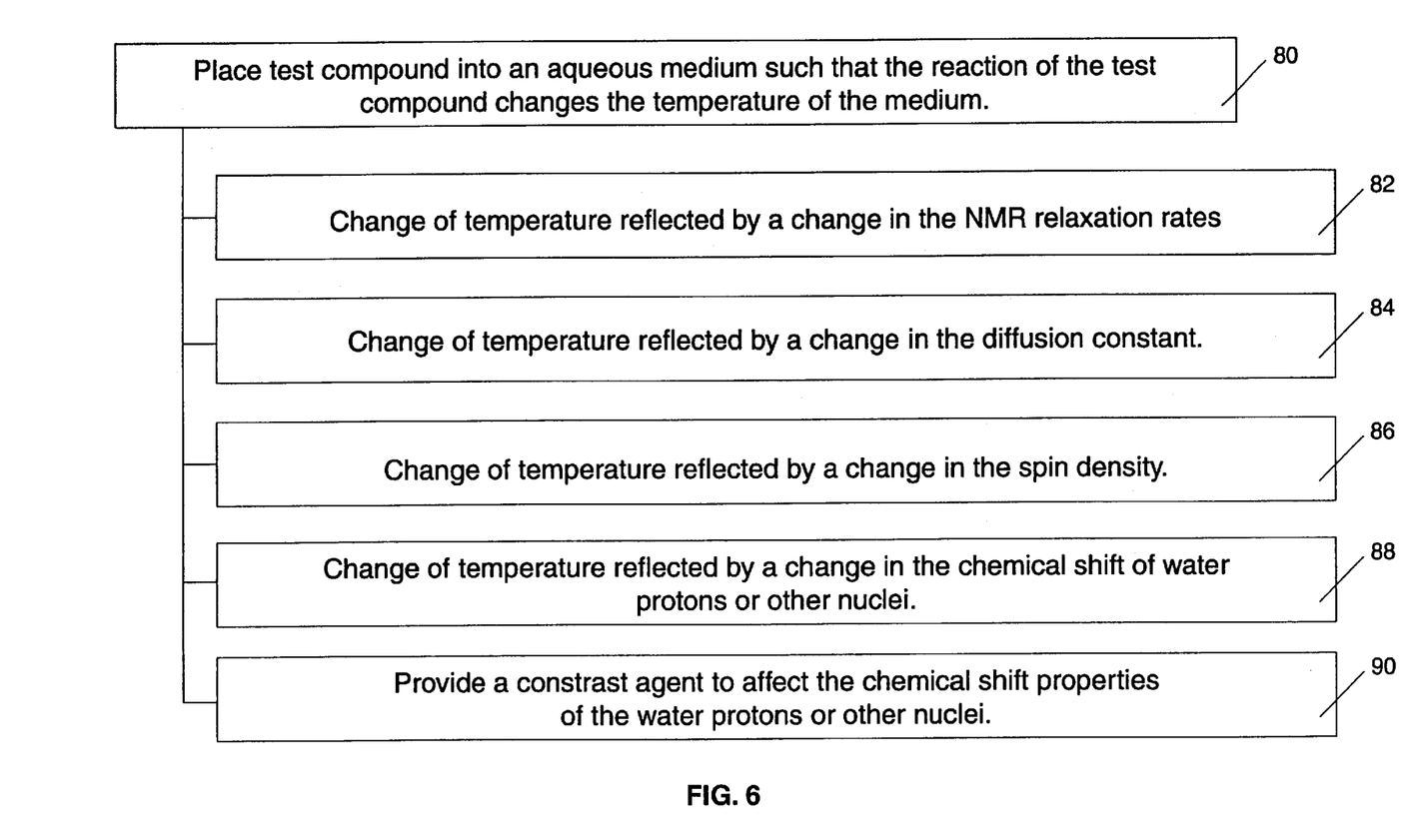
FIG. 6 is a diagram illustrating various assays where reaction of a test compound changes the temperature of the medium, with the change in temperature being detectable by nuclear magnetic resonance according to the invention.

As shown in FIG. 6, assays may be configured so that biological activity of a test compound changes the temperature of the medium. For example, as shown in step 80, the test compound may be placed into an aqueous medium, where reaction of the test compound in the mixture changes the temperature of the medium. In turn, the change in temperature may be measured using nuclear magnetic resonance to indicate that the test compound is biologically active.

As shown in steps in 82, 84 and 86, the change in temperature may be reflected by a change in the NMR relaxation rates, diffusion constant or spin density of the water protons or other nuclei in the aqueous medium. As shown in step 88, the change in temperature may alternatively be reflected by a change in the chemical shift of water protons or other nuclei in the aqueous medium. Optionally, as shown in step 90, the aqueous medium may contain a contrast agent that affects the chemical shift properties of the water protons or other nuclei in a manner that is reflective of temperature. Examples of contrast agents that may be used include those agents containing a lanthanide metal, such as Ce, Pr, Nd, Sm, Eu, Gd, Db, Dy, Ho, Er, Tm, and Yb. One specific contrast agent that may be utilized comprises Pr [MOE-DO3A].

Figure 7A:
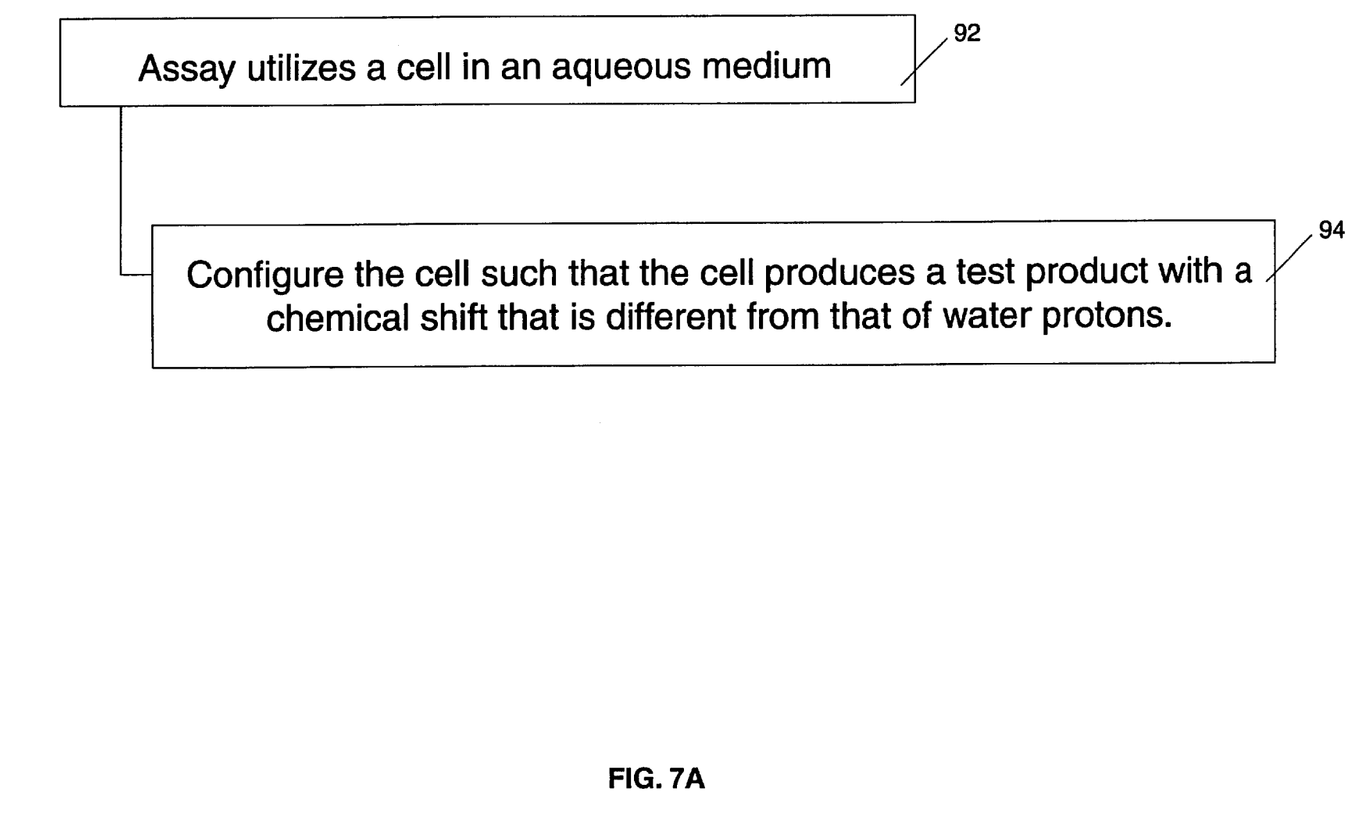
FIG. 7A is a diagram illustrating various assays where a cell in an aqueous medium is configured to produce a test product with a chemical shift different from that of water.

As illustrated in step 92 of FIG. 7A, the assay may utilize a cell within an aqueous medium. As shown in step 94, the cell may be configured so that it will produce a test product having a chemical shift that is different from that of water protons to indicate that the test product is biologically active. Hence, the invention may utilize cells or other entities that produce a test product which may then be evaluated using NMR. Examples of test products that may be produced using the assays of the invention include choline, lactate, N-acetyl-aspartate, N-acetyl-glutamate, ATP, ADP, alanine, creatine, phosphol-creatine, phosphocholine, citrate, myo-inositol, methanol, ethanol, and the like. The test product may be produced as part of a cell reporter system to evaluate test compounds. The test product may also be produced constitutively to evaluate different cell lines and enzymes that they produce.

Figure 7B:
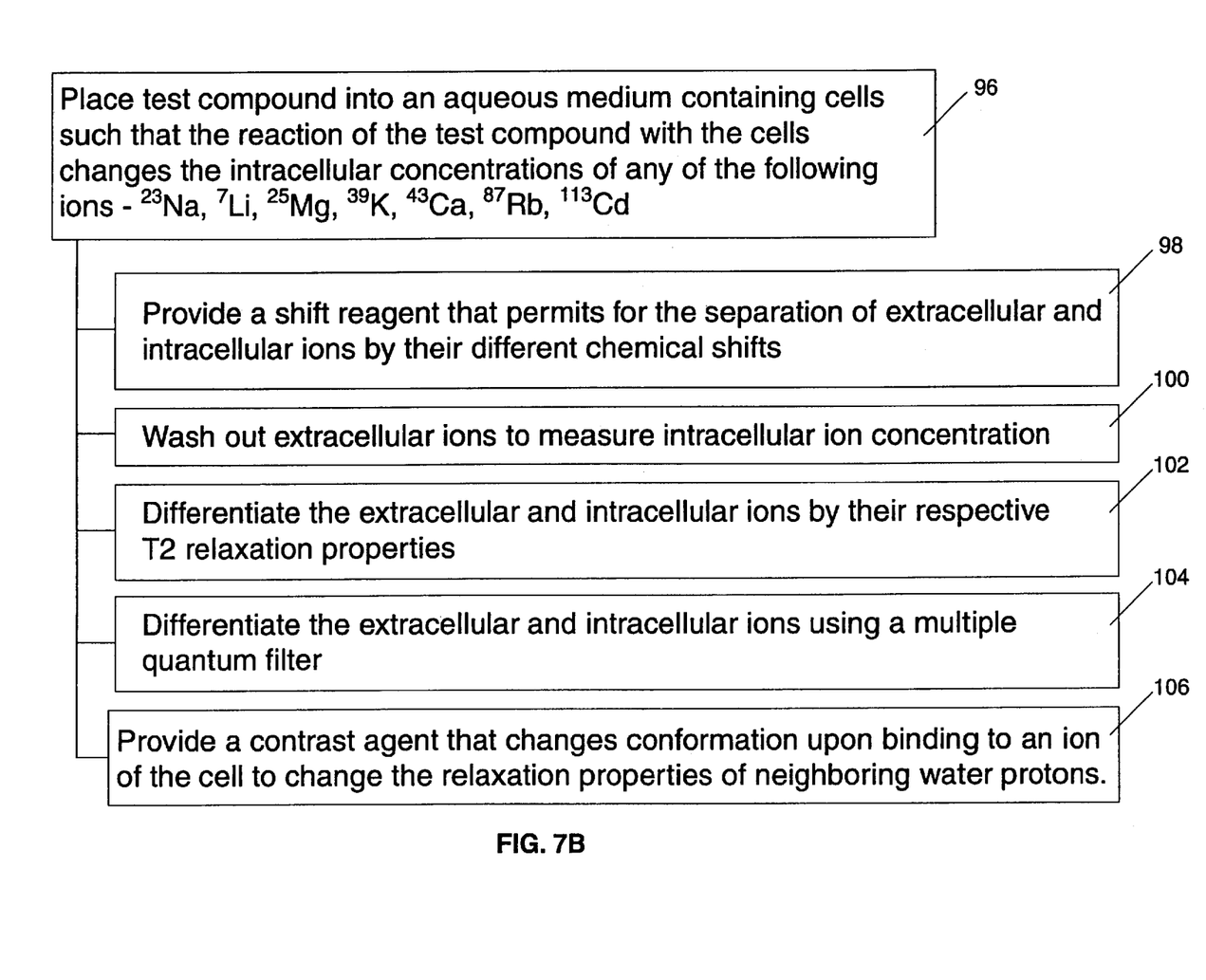
FIG. 7B is a diagram illustrating various assays for compounds that are either ion channel agonists or antagonists and thus change intracellular ion concentrations, with the concentration changes being detectable with nuclear magnetic resonance according to the invention.

As shown in step 96 of FIG. 7B, a test compound may be combined with a cell that, when reacting with a test compound, causes the intracellular concentration of one or more ions to change in a manner that is detectable by NMR. Examples of ions that may be utilized include $^{23}Na$, $^7Li$, $^{25}Mg$, $^{39}K$ $^{43}Ca$, $^{87}Rb$, $^{113}Cd$, and the like.

Block 98 illustrates a means by which the intracellular and extracellular ions are separated by their chemical shifts. The chemical shift separation has been induced by the addition of a shift reagent that comes in contact with only the extracellular ions. Examples of shift reagents that may be used include those reagents containing a lanthanide metal, such as Ce, Pr, Nd, Sm, Eu, Gd, Db, Dy, Ho, Er, Tm, and Yb. Exemplary shift reagents that may be employed include $Dy(PPP)_2^{7-}$-dysprosium tripolyphosphate, $Tm(DOTP)^{5-}$, the thulium (III) complex of 1,4,7,10-tetraazacylododecane-N,N',N'',N'''-tetra(methylenephospate), $Dy(DPA)_3^{3-}$-dysprosium dipicolinate pyridine-2,6-dicarboxylate, $Dy(NTA)_2^{3-}$, dysprosium nitrilotriacetate, $Dy(TTHA)^{3-}$-dysprosium triethylenetetraminehexaacetate, $Tm(PPP)_2^{7-}$, and $Tm(TTHA)^{3-}$. As shown in steps 100 and 102, the extracellular and intracellular ions may be differentiated by their T2 relaxation properties or through the use of a multiple quantum filter. Optionally, as shown in block 100, the extracellular ions may be washed out, while still maintaining the osmotic potential so that the NMR signal emanates from only the intracellular ions.

Another alternative to differentiating the extra- and intracellular ion pools is to use a T2-based filter as shown in block 102. Alternatively, as shown in block 104, a multiple quantum filter may be used. Block 106 shows another technique for measuring ion concentration via the introduction of a contrast agent that changes conformation upon binding to an ion in the mixture. When binding to the ion, the relaxation properties of nearby water protons are changed and may be detected using NMR. Examples of contrast agents that may be used include those containing a lanthanum metal such as Ce, Pr, Nd, Sm, Eu, Gd, Db, Dy, Ho, Er, Tm, and Yb, or another paramagnetic element, Such as Fe, Mn and the like. One particular contrast agent that may be utilized comprises DOPTA-Gd.

Figure 8:
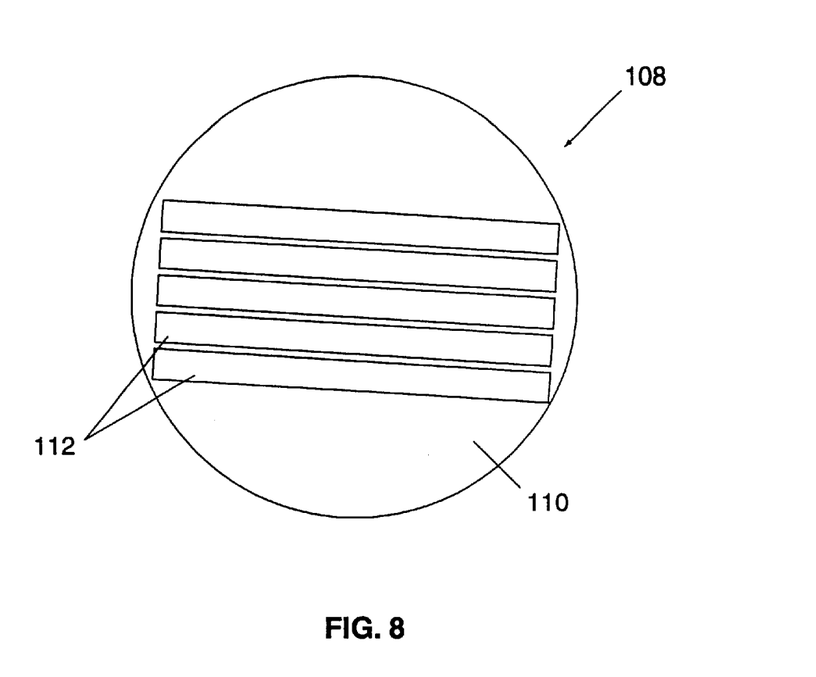
FIG. 8 illustrates an arrangement of multi-well plates that may be used in a nuclear magnetic resonance device when screening chemicals according to the invention.

Referring now to FIG. 8, an exemplary system 108 for holding a test compound or product when screening using NMR will be described. System 108 comprises a generally spherical body 110 that is formed about a plurality of multi-well plates 112 that are stacked on top of each other. Use of spherical body 110 helps minimize spatial distortions and signal loses during imaging. Alternatively, body 110 may be constructed to be cylindrical in geometry.

Body 110 is constructed so that it contacts all of the exterior surfaces of plates 112 to eliminate air or other gases within body 110. Conveniently, body 110 and plates 112 may be constructed of a material with desired magnetic susceptibility properties to minimize spatial distortions and signal loses. Examples of materials that may be used include polystyrene, polycarbonate and polypropylene.

Figure 9:
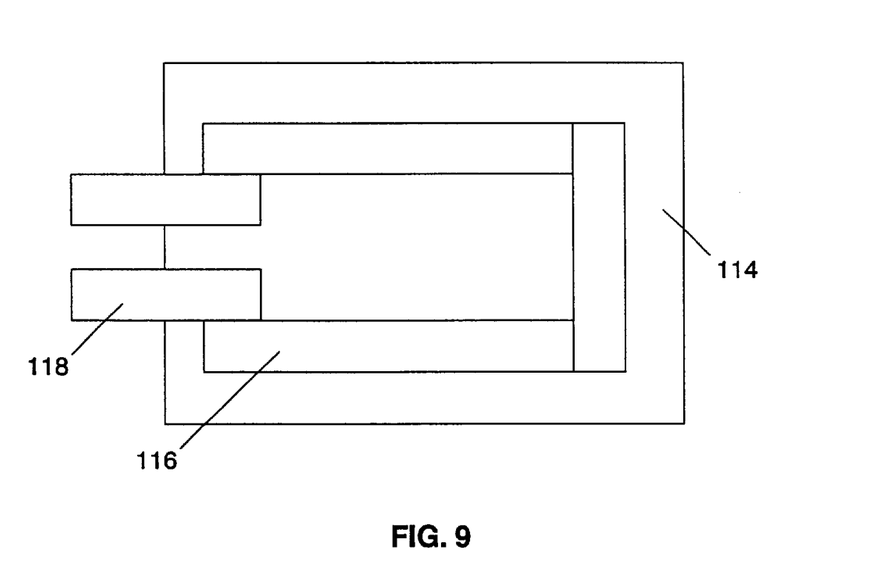
FIG. 9 illustrates a multi-well plate system having a RF coil that may be used in a nuclear magnetic resonance device according to the invention.

FIG. 9 is a side view of a cylindrical container 114 for holding multi-well plates in a manner similar to that described above. A RF saddle coil 116 is integrated into container 114. A connector 118 is provided to permit RF coil 116 to be coupled to a magnetic resonance imaging system. As such, a separate RF coil may not be needed in the imaging system.

Figure 10A:
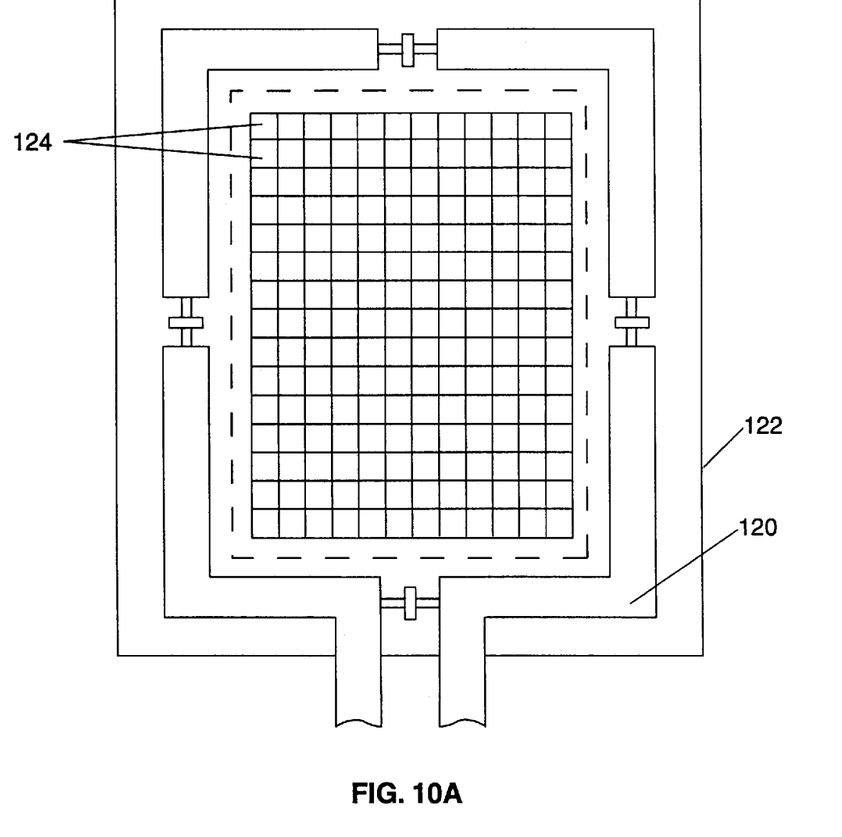
FIG. 10A is a top view of a multi-well plate and an accompanying RF coil according to the invention.

FIG. 10A illustrates an alternative way to utilize an RF coil 120 in connection with a multi-well plate 122. Plate 122 includes a plurality of wells 124 that are surrounded by RF coil 120. Conveniently, RF coil 120 may be configured to be detachable from plate 122 so that the plate may be disposed following use and RF coil 120 reused. For example, plate 122 may include a channel or trough into which RF coil 120 may be positioned. Following use, RF coil 120 may simply be removed and reused with a similar multi-well plate.

Figure 10B:
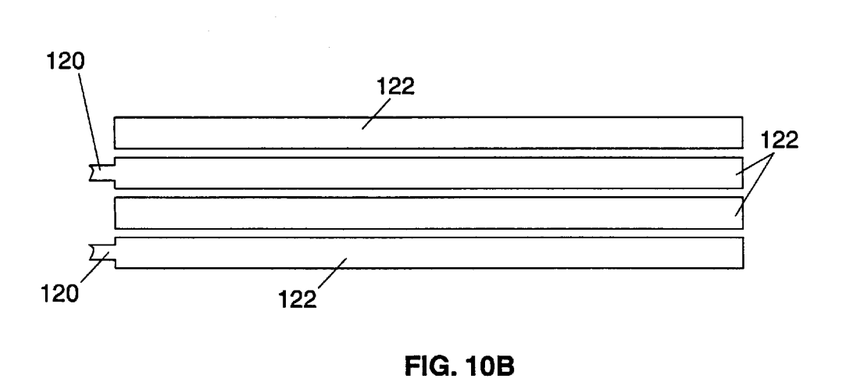
FIG. 10B is a side view of a stack of multi-well plates, some of which include an RF coil according to the invention.

As shown in FIG. 10B, multiple multi-well plates 122 may be stacked on top of each other when used within an MRI system. As shown, two of the multi-well plates include RF coils 120. However, it will be appreciated that other arrangements of RF coils may be used. For example, when stacked upon each other only a single RF coil may be needed, or alternatively, multiple RF coils may be provided.

Figure 11:
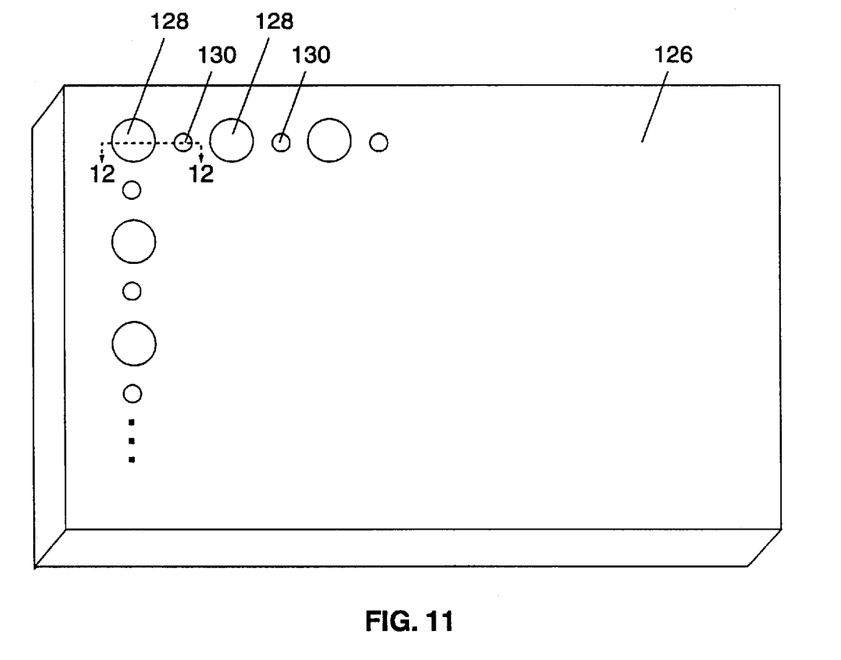
FIG. 11 illustrates a plate having a plurality of sample chambers that may be filled in a manner such that substantially all air is removed from the sample chambers according to the invention.

Shown in FIG. 11 is a plate 126 having a plurality of conical sample chambers 128 (only a few being shown for convenience of illustration) for receiving liquid samples. As described hereinafter, plate 126 is constructed so that it will be essentially void of any air or other gas bubbles following introduction of the samples into sample chambers 128. In this way, spatial distortions and signal losses will be minimized during screening.

Figure 12A:
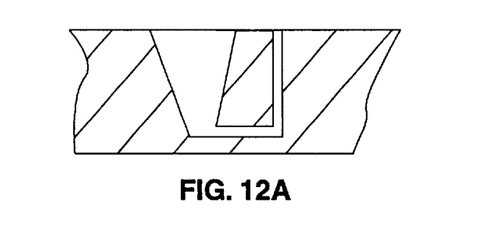
FIGS. 12A–12C illustrate one method for filling the sample chambers of the plate of FIG. 11.
Figure 12B:
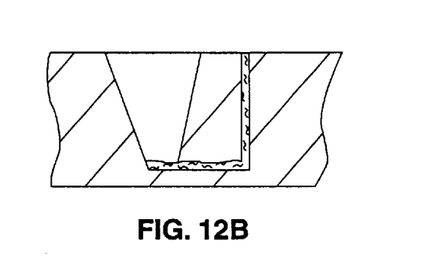
Figure 12C:
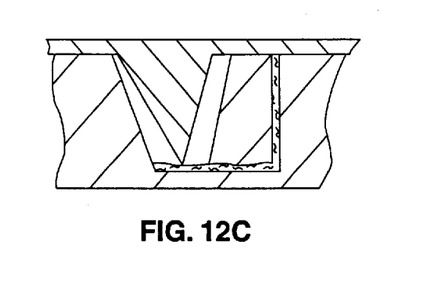

As also shown in FIG. 12A, each sample chamber 128 is in fluid communication with a vent 130. When a sample 132 is deposited within sample chamber 128, it will fill the bottom of chamber 128 and move upwardly through vent 130 by capillary forces as shown in FIG. 12B. When the sample chambers have received their samples, a cover 134 is placed over plate 126 as shown in FIG. 12C. Cover 134 includes a plurality of conical sections 136 that fit within sample chambers 126. Due to their conical shape, air or other gases are permitted to escape from chambers 128 when cover 134 is placed onto plate 126. Hence, when cover 134 is in place, essentially no air or other gases are present within plate 126 to facilitate imaging as previously described.

The invention has now been described in detail for purposes of clarity and understanding. However, it will be appreciated that certain changes and modifications may be practiced within the scope of the appended claims.

What is claimed is:

1. A screening method comprising:
   performing an assay in which one or more chemicals and/or entities are present in a mixture to produce an outcome;
   applying a static magnetic field ($B_0$) to the mixture;
   applying one or more RF magnetic pulses to the mixture; and
   measuring and evaluating resulting FID or echo signals to evaluate the outcome of the assay.

2. A method as in claim 1, further comprising performing the assay in a plate having a plurality of wells, wherein the mixture in each well includes a different chemical and/or entity, and further comprising applying spatially dependent $B_0$ gradient fields to the wells and measuring and evaluating FID or echo signals from the wells.

3. A method as in claim 1, wherein the mixture includes a test compound that causes a detectable nuclear magnetic resonance signal to be produced that is dependent on the degree of interaction of the test compound with the mixture.

4. A method as in claim 3, wherein the test compound comprises a test product, and wherein the entities includes one or more cells that produce the test product.

5. A method as in claim 2, wherein the different entities comprise cells which produce a test product with a chemical shift different from that of water protons.

6. A method as in claim 5, wherein the test product is selected from a group of products consisting of choline, lactate, N-acetyl-aspartate, N-acetyl-glutamate, ATP, ADP, alanine, creatine, phosphocreatine, phosphocholine, citrate, myo-inositol, methanol, and ethanol.

7. A method of screening comprising:
   combining a test compound with another chemical and/or entity to form a mixture, wherein the test compound causes a detectable nuclear magnetic resonance signal to be produced that is dependent on the amount of interaction of the test compound with the mixture;
   applying a static magnetic field ($B_0$) to the mixture;
   applying one or more RF magnetic pulses to the mixture; and
   measuring and evaluating resulting FID or echo signals to obtain information as to whether the test compound is biologically active in the mixture.

8. A method as in claim 7, wherein different test compounds are provided in multiple wells, and further comprising applying spatially dependent $B_0$ gradient fields to the wells, and measuring and evaluating the FID or echo signals from each of the wells at substantially the same time.

9. A method as in claim 8, wherein the wells are arranged in a three dimensional array.

10. A method as in claim 7, wherein the combining step further comprises combining the test compound with at least one cell in an aqueous medium, wherein the test compound is biologically active when binding to a receptor on the cell surface or within the cell to produce an enzyme that indirectly affects the relaxation properties of water protons to indicate that the test compound is biologically active.

11. A method as in claim 10, wherein the enzyme modifies the relaxation properties of water protons by cleaving a probe molecule in the mixture, thereby increasing the exposure of a paramagnetic atom in the probe molecule to water protons and decreasing the T1 relaxation rate of the water protons.

12. A method as in claim 11, wherein the enzyme comprises beta-galactosidase and the probe molecule comprises a chelated gadolinium atom complexed with a galactose molecule, whereby the galactosidase causes the galactose molecule to be cleaved from the chelated gadolinium.

13. A method as in claim 7, wherein the combining step further comprises mixing the test compound in an aqueous medium with a chemical or entity that when reacting with the test compound changes the pH of the medium, and wherein the change is measurable using nuclear magnetic resonance to indicate that the test compound is biologically active.

14. A method as in claim 13, wherein the change in pH of the aqueous medium causes a change to the ionization of polymer molecules also in the aqueous medium, thereby changing the viscosity of the aqueous medium and affecting nuclear magnetic resonance relaxation properties, magnetization transfer properties, spin density and/or the diffusion coefficient of the water protons constituting the aqueous medium.

15. A method as in claim 13, wherein the change in pH of the aqueous medium causes a change to the volume or configurations of gel particles also in the medium, thereby affecting nuclear magnetic resonance relaxation properties, magnetization transfer properties, spin density and/or the diffusion coefficient of the water protons constituting the aqueous medium.

16. A method as in claim 13, wherein the aqueous medium contains a pH-sensitive contrast agent that causes the nuclear magnetic resonance relaxation properties of water protons or other nuclei constituting the aqueous medium to be changed in a manner that is reflective of pH.

17. A method as in claim 16, wherein the contrast agent contains a lanthanide metal selected from a group consisting of Ce, Pr, Nd, Sm, Eu, Gd, Tb, Dy, Ho, Er, Tm, and Yb or another paramagnetic element selected from a group consisting of Fe, Mn or $^{17}O$.

18. A method as in claim 17, wherein the contrast agent comprises Fe(III)meso-tetra(4-sulfonatophenyl)porphine (Fe-TPPS4).

19. A method as in claim 17, wherein the contrast agent comprises $H_2^{17}O$.

20. A method as in claim 13, wherein the aqueous medium comprises water protons or other nuclei, and wherein the aqueous medium contains a shift reagent affecting the chemical shift properties of the water protons or other nuclei in a manner that is reflective of pH.

21. A method as in claim 20, wherein the shift reagent contains a lanthanide metal selected from a group consisting of Ce, Pr, Nd, Sm, Eu, Gd, Tb, Dy, Ho, Er, Tm, and Yb or another paramagnetic element.

22. A method as in claim 21, wherein the shift reagent comprises $Tm(DOTP)^{5-}$, the thulium (III) complex of 1,4,7,10-tetraazacylododecane-N,N',N'',N'''-tetra (methylenephospate).

23. A method as in claim 21, wherein the shift reagent comprises $Dy(PPP)_2^{7-}$-dysprosium tripolyphosphate.

24. A method as in claim 7, wherein the combining step further comprises placing the test compound into an aqueous medium, and wherein the chemical and/or entity is selected such that when reacting with the test compound changes the temperature of the medium, and wherein the temperature is measurable using nuclear magnetic resonance to indicate that the test compound is biologically active.

25. A method as in claim 24, wherein the aqueous medium comprises water protons, and wherein the change in temperature of the aqueous medium is reflected by a change in the nuclear magnetic resonance relaxation rates, diffusion constant or spin density of the water protons.

26. A method as in claim 24, wherein the aqueous medium comprises water protons or other nuclei, and wherein the change in temperature of the aqueous medium is reflected by a change in the chemical shift of the water protons or other nuclei.

27. A method as in claim 24, wherein the aqueous medium comprises water protons or other nuclei, and wherein the aqueous medium contains a contrast agent affecting the chemical shift properties of the water protons or other nuclei in a manner that is reflective of temperature.

28. A method as in claim 27, wherein the contrast agent contains a lanthanide metal selected from a group consisting of Ce, Pr, Nd, Sm, Eu, Gd, Tb, Dy, Ho, Er, Tm, Yb.

29. A method as in claim 28, wherein the contrast agent comprises Pr[MOE-DO3A].

30. A method as in claim 7, wherein the entity comprises a cell in an aqueous medium, and wherein the cell is configured to produce a test product that has a chemical shift different from that of water protons to indicate that the compound is biologically active.

31. A method as in claim 30, wherein the test product comprises a molecule that is selected from a group consisting of choline, lactate, N-acetyl-aspartate, N-acetyl-glutamate, ATP, ADP, alanine, creatine, phosphocreatine, phosphocholine, citrate, myo-inositol, methanol, and ethanol.

32. A method as in claim 7, wherein the mixture includes an aqueous medium, and wherein the combining step comprises combining the test compound with a cell that when reacting with the test compound causes the concentration of one or more intracellular ions to change in a manner that is detectable by nuclear magnetic resonance.

33. A method as in claim 32, wherein the intracellular ions are selected from a group consisting of $^{23}Na$, $^{7}Li$, $^{25}Mg$, $^{39}K$, $^{43}Ca$, $^{87}Rb$ or $^{113}Cd$.

34. A method as in claim 7, wherein the mixture includes one or more cells in an aqueous medium, and wherein the aqueous medium contains a shift reagent allowing for separation of extracellular and intracellular ions by their different chemical shifts.

35. A method as in claim 34, wherein the shift reagent contains a lanthanide metal selected from a group consisting of Ce, Pr, Nd, Sm, Eu, Gd, Tb, Dy, Ho, Er, Tm, Yb.

36. A method as in claim 35, wherein the shift reagent is selected from a group consisting of $Dy(PPP)_2^{7-}$-dysprosium tripolyphosphate, $Tm(DOTP)^{5-}$, the thulium (III) complex of 1,4,7,10-tetraazacylododecane-N,N',N'',N'''-tetra (methylenephospate), $Dy(DPA)_3^{3-}$-dysprosium dipicolinate pyridine-2,6-dicarboxylate, $Dy(NTA)_2^{3-}$, dysprosium nitrilotriacetate, $Dy(TTHA)^{3-}$-dysprosium triethylenetetraminehexaacetate, $Tm(PPP)_2^{7-}$, and $Tm(TTHA)^{3-}$.

37. A method as in claim 34, wherein the extracellular and intracellular ions are differentiated by their T2 relaxation properties.

38. A method as in claim 34, wherein the extracellular and intracellular ions are differentiated by the use of a multiple quantum filter.

39. A method as in claim 34, further comprising washing the extracellular ions out of the aqueous medium before nuclear magnetic resonance measurements are made.

40. A method as in claim 7, wherein the mixture includes an aqueous medium comprising water protons, and further comprising introducing a contrast agent to the aqueous medium that changes conformation upon binding to an ion in the mixture, thereby changing the relaxation properties of the water protons.

41. A method as in claim 40, wherein the contrast agent contains a lanthanide metal selected from a group consisting of Ce, Pr, Nd, Sm, Eu, Gd, Tb, Dy, Ho, Er, Tm, Yb or other paramagnetic element selected from a group consisting of Fe and Mn.

42. A method as in claim 41, wherein the contrast agent comprises DOPTA-Gd.

43. A method of screening comprising:
  providing a plurality of plates that each include multiple wells;
  introducing a chemical and/or entity into at least some of the wells of each plate;
  introducing a test compound into wells containing the chemical and/or entity;
  stacking the plates on top of each other; and
  inserting the plates into a nuclear magnetic resonance device and screening for any biologically active test compounds.

* * * * *